United States Patent [19]

Smeltzer et al.

[11] 4,354,327

[45] Oct. 19, 1982

[54] TISSUE CULTURE METHOD FOR ASEXUAL PROPAGATION OF PINE TREES AND MEDIUM FOR USE THEREWITH

[75] Inventors: Richard H. Smeltzer, Natchez, Miss.; Linda M. Cello, Southfields, N.Y.

[73] Assignee: International Paper Company, New York, N.Y.

[21] Appl. No.: 33,915

[22] Filed: Apr. 27, 1979

[51] Int. Cl.³ .............................................. A01G 1/00
[52] U.S. Cl. ........................................................ 47/58
[58] Field of Search ............................................ 47/58

[56] References Cited

U.S. PATENT DOCUMENTS 4,038,778  8/1977  Kadkade ................................. 47/58
4,152,869  5/1979  Jones ...................................... 47/58

OTHER PUBLICATIONS

Stimulation of adventitious . . . , Heide, Nature, 219, 1968, pp. 960–961.
Interaction of abscisic acid . . . , Basu et al., Plant and Cell Physiol., 47, 1971, pp. 681–684.
Differention of plantlets . . . , Sommer et al., Bot. Gaz., 136, 1970, pp. 196–200.
Promotion of callus . . . , Altman et al., Plant Physiol., 47, 1971, 844–846.
Development and differentiation . . . , Gresshof et al., Planta (Berlin), 107, 1972, pp. 161–170.
The effects of abscisic . . . , Ammirato, Bot. Gaz., 135 (4), 1974, pp. 328–337.
Induction of multiple buds . . . , Campbell et al., Can. J. Bot., 53, 1975, pp. 1652–1657.
Adventitious bud formation . . . , Cheng, Plant Sci. Letters, 5, 1975, pp. 97–102.
Vegetative propagation . . . , Campbell et al., Can. J. For. Res., 6, 1976, pp. 240–243.
Production of forest trees . . . , Mott et al., TAPPI, 60, No. 6, 1977.
Shoots from Douglas-Fir cultures, Can. J. Bot., 55, No. 9, 1977, pp. 1246–1250.
Hormonal Control of . . . , Mehra-Palta et al., TAPPI, 61, No. 1, 1978.

*Primary Examiner*—Robert E. Bagwill
*Attorney, Agent, or Firm*—Richard J. Ancel

[57] ABSTRACT

A tissue culture method for the asexual propagation of pine trees is described and claimed. The method involves promoting adventitious buds from pine seeds by inoculating decoated seeds that have been previously stimulated to germinate in a culture medium. The method enhances adventitious bud formation and is operationally more practical than currently reported methods in that it is neither time consuming nor labor intensive. Also, novel culture media are described and claimed which employ the interaction of the growth regulators benzylaminopurine and abscisic acid.

14 Claims, No Drawings

TISSUE CULTURE METHOD FOR ASEXUAL PROPAGATION OF PINE TREES AND MEDIUM FOR USE THEREWITH

BACKGROUND OF THE INVENTION

This invention relates to a tissue culture method for the asexual propagation of pine or coniferous trees, said method includes producing multiple adventitious buds from seeds as an essential step.

The current practice of asexual propagation of pine trees through tissue culture requires, as the explant source, embryonic tissue excised from seeds or the use of tissue from young seedlings. From an operational viewpoint, older tissue culture methods, as applied to seed tissues, are unacceptable because of the time and tedious manual labor associated with excising embryonic tissue. Additionally, such methods suffer in that multiple adventitious buds from excised embryonic tissue, as required for asexual propagation, are induced only after a minimum of four weeks.

For example, according to H. E. Sommer, et al., Differentiation of Plantlets in Longleaf Pine (PINUS PALUSTRIS MILL) Tissue Cultured in Vitro, Bot. Gaz., 136, at pp. 196-200 (1970), embryos were dissected from surfaced sterilized seeds of longleaf pine. Thereafter, the embryos were grown in tissue culture media for four to six weeks. Signs of adventitious bud initiation appeared only after four weeks. Similarly, Tsai-Ying Cheng, Adventitious Bud Formation in Culture of Douglas Fir (PSEUDOTSUGA MENZIESII (MIRB) FRANCO), Plant Science Letters, 5, at pp. 97-102 (1975), reports that embryos excised from sterilized decoated seeds of Douglas-fir produced excisable adventitious buds in a tissue culture method after four weeks. These two references are hereby incorporated by reference.

It is known to modify otherwise conventional tissue culture media, comprising standard nutrients, to produce a desired effect. For example, such modification includes adding specified amounts of one or more of the following growth regulators: benzylaminopurine (6-benzylaminopurine), zeatin, 6-$\gamma$,$\gamma$-dimethylallylaminopurine, kinetin, abscisic acid, indole-3-acetic acid, $\gamma$-indolebutyric acid and $\gamma$-naphthaleneacetic acid. For example, Asha Mehra-Palta, Richard H. Smeltzer and Ralph L. Mott, "Hormonal control of induced organogenesis," Experiments with excised plant parts of loblolly pine, TAPPI, 61, No. 1, (1978), describe a tissue culture media containing suitable nutrients, modified by the addition of one or more of the following, as growth regulators: benzylaminopurine, zeatin, 6-$\gamma$,$\gamma$-dimethylallylaminopurine, kinetin and $\gamma$-naphthaleneacetic acid. A synergistic effect was attributed to media containing $\gamma$-naphtaleneacetic acid, at a low concentration, and one other growth regulator. R. N. Basu et al., "Interaction of Abscisic Acid and Auxins in Rooting of Cuttings, Plant & Cell. Physical., 11, 681-684 (1970), report that abscisic acid at optimum concentrations promoted rooting of PHASEOLUS AUREUS ROXB. and LYCOPERSICON ESCULENTUM MILL. stem cuttings. A synergistic effect of abscisic acid was noted on $\gamma$-indolebutyric acid-induced rooting of LYCOPERSICON cuttings. Abscisic acid was suggested as a potential important natural regulator or rooting in cuttings. Arie Altman et al., Promotion of Callus Formation by Abscisic Acid in Citrus Bud Cultures, Plant Physical., 47, 844-846 (1971) report that abscisic acid promoted callus formation in explants of citrus plants. Additionally, benzylaminopurine demonstrated no synergistic effect on abscisic acid-induced callus formation, although other growth regulators produced such an effect. Altman et al, reported culture medium containing benzylaminopurine at a concentration of 218 mg./l and abscisic acid at a concentration of 264 mg./l. Each of these three references are hereby incorporated by reference.

SUMMARY OF THE INVENTION

A tissue culture method for the asexual propagation of coniferous trees that overcome shortcomings associated with previously reported methods and novel culture media utilized therewith have now been discovered. Said method includes producing multiple adventitious buds from seeds as an essential step. Such buds are suitable for rooting to accomplish asexual propagation.

This method employs stimulating seed germination and seed decoating. Because the decoating of seeds is neither time consuming nor labor intensive, operational problems associated with excising embryos are solved. Remarkably, formation of multiple adventitious buds, sufficient for asexual propagation or cloning, has been induced in less time by the present decoated seed technique.

The novel culture media of this invention contain growth regulators, abscisic acid (ABA) and benzylaminopurine (BAP). Apparently, ABA inhibits vegetative growth and enhances the ability of BAP to induce bud formation. A high frequency of stimulated decoated seeds can provide multiple adventitious bud formation in as little as two weeks' time when inoculated on such a culture medium. Surprisingly, the effect of our novel culture media on bud formation appears more pronounced with stimulated decoated seeds than with excised embryos or portions thereof.

The tissue culture method and culture media described and claimed herein are particularly well suited for inducing multiple buds from embryonic tissue of loblolly pine. Since the method solves problems associated with previously known methods, it may be used in the forestry industry to multiply the progeny from superior trees.

DETAILED DESCRIPTION OF THE INVENTION

Broadly, this invention relates to a novel tissue culture method for the asexual propagation or cloning of pine or coniferous trees and to culture media utilized therewith. Said method involves producing multiple adventitious buds from seed as an essential step. This invention is particularly suited for use in connection with loblolly pine trees.

The method described and claimed herein involves stimulation of pine seeds toward germination, seed coat removal, and inoculating the nucellar tissue on a culture medium. The culture medium contains the growth regulator BAP and, preferably, a second growth regulator ABA. Pine seeds treated according to the method of this invention produce multiple adventitious buds have been rooted to provide as many as ten plants from a single seed.

Stimulation of the pine seeds is a relatively simple operation consisting of making a root end or micropilar cut into the endosperm of the seed, and then immersing the seeds in a dilute hydrogen peroxide solution. Preferably, about 1% hydrogen peroxide is employed and immersion is continued for one week. It is recommended to replace the hydrogen peroxide after each two or three days to insure uniform germination and minimize the risk of contamination by microorganisms. 1 ml. of hydrogen peroxide should be used for each seed.

Following growth stimulation, the seeds are decoated. Seed decoating can be accomplished by a relatively simple manual operation. Root radical emergence from the seed, produced in the stimulation process, splits the seed coat along its line of symmetry. The resulting halves of the split seed coat can be removed easily from the nucellar tissue with a thumbnail.

The nucellar tissue or decoated seeds should be surface sterilized prior to inoculation in the culture medium. In this regard, sodium hypochlorite or calcium hypochlorite are suitable sterilizing agents. Following sterilization the nucellar tissue should be washed with water. These operations are established procedures in the practice of tissue culture. For example, such operations are mentioned by Tsa-Ying Cheng in the reference cited earlier.

For best results, nucellar tissue should be inoculated into the culture medium by inserting the protruding root radical into the medium.

Culture media employed in our method are basically conventional media, known to those skilled in the art, as modified by the introduction of the growth regulator BAP and, preferably, a second growth regulator ABA. For example, Peter M. Gresshoff et al., Development and Differentiation of Haploid LYCOPERSICON ESULENTUM (Tomato), Planta (Berl.) 107, 161-170 (1972) and Harry E. Sommer et al., Differentiation of Plantlets in Longleaf Pine (PINUS PALUSTRIS MILL.) Tissue Cultured In Vitro, Bot. Gaz., 136, 196-200 (1970), each of which are hereby incorporated by reference, mention such conventional media. The frequency of embryos producing buds can be increased by either raising the concentration of BAP in the medium or by maintaining BAP constant and adding relatively small amounts of ABA. Apparently, ABA inhibits vegetative growth which enhances the ability of BAP to promote bud formation. Preferred media contain BAP at a concentration equal to or greater than 10 mg./l and ABA at a concentration of from about 0 to about 3.0 mg./l. Especially preferred media contain about 20 mg./l BAP and 0.03 mg/l ABA. Increasing the concentration of BAP higher than about 20 mg./l, at any given concentration of ABA, did not result in substantial improvement of bud formation.

Physical conditions to which the seed inoculated culture media are subjected are not critical. However, constant light is desirable and temperatures suitable for maintaining vegetative growth are preferred.

The tissue culture method and culture media of this invention is illustrated further by the following non-limiting examples.

Loblolly pine seeds were cut on their micropilar or root end into the endosperm. The cut seeds were immersed in 1% hydrogen peroxide (1 ml/seed) for one week with a change of the hydrogen peroxide after each two days. The temperature of the hydrogen peroxide is maintained at 21°-27° C. throughout. Thereafter, seed coats were removed manually and the nucellar tissue was surface-sterilized by immersion in a 10% Clorox ® (a trademark owned by the Clorox company for sodium hypochlorite) solution for 10 minutes. The surface-sterilized decoated seeds were rinsed twice with sterile water, a ten minute sterile water soak between rinses. Then the sterile decoated seeds were inoculated into the culture media by inserting the protruding root radical into the media. The media used was as follows:

| Composition of the Bud Induction Medium | |
|---|---|
| Compound | Concentration (mg./l) |
| $(NH_4)_2SO_4$ | 100 |
| $CaCl_2.2H_2O$ | 75 |
| $MgSO_4.7H_2O$ | 125 |
| $KNO_3$ | 500 |
| $KCl$ | 150 |
| $KI$ | 0.375 |
| $NaH_2PO_4.H_2O$ | 45 |
| $Na_2HPO_4$ | 15 |
| $FeSO_4.7H_2O$ | 13.9 |
| $NA_2EDTA$ | 18.6 |
| $MnSO_4.H_2O$ | 5.0 |
| $ZnSO_4.7H_2O$ | 1.5 |
| $H_3BO_3$ | 1.5 |
| $CuSO_4.5H_2O$ | 0.125 |
| $NaMoO_4.2H_2O$ | 0.125 |
| $CoCl_2.6H_2O$ | 0.125 |
| myo-Inositol | 5.0 |
| Thiamine HCl | 0.5 |
| Nicotinic Acid | 0.05 |
| Pyridoxine HCl | 0.05 |
| ABA | 0 to 30.0 |
| BAP | 0 to 50 |
| Sucrose | 20,000 |
| Agar | 9,000 |

The media was adjusted to pH 5.6 and solidified with 0.9% Difco Bacto ® agar. Cultures were maintained in sealed test tubes and exposed to constant illumination with Westinghouse 40-W F40/AGRO-light (2400-3200 lux incident light). The temperature was maintained at approximately 22° C.

After two to six weeks in culture, adventitious buds formed on the cotyledons and occasionally hypocotyl of developing embryos of decoated cultured on media containing BAP and ABA.

Tables 1 and 2 shown the percentage of culture forming adventitious buds after two and five weeks, respectively;

Table 3 shows the bud induction effect of high levels of BAP;

Table 4 shows the results of buds induction after 40 days; and

Table 5 shows the time course of bud induction.

TABLE I

BUD INDUCTION RESPONSES OF DECOATED SEEDS AT TWO WEEKS - PERCENTAGE OF EMBRYOS WITH BUDS

| BAP, mg/l | ABA, mg/l | | | | |
|---|---|---|---|---|---|
| | 0 | 0.03 | 0.3 | 3.0 | 30.0 |
| 0 | 0 | 10 | 0 | 12 | 0 |
| 1 | 0 | 10 | 10 | 12 | 11 |
| 10 | 30 | 33 | 40 | 12 | 33 |
| 20 | 40 | 70 | 33 | 22 | 0 |

TABLE 2

Bud Induction Responses of Decoated Seeds at Five Weeks - Percentage of Embryos with Buds

| BAP, mg/l | ABA, mg/l | | | | |
|---|---|---|---|---|---|
| | 0 | 0.03 | 0.3 | 3.0 | 30.0 |
| 0 | 0 | 20 | 0 | 12 | 0 |
| 1 | 10 | 30 | 50 | 50 | 11 |

TABLE 2-continued

Bud Induction Responses of Decoated Seeds at
Five Weeks - Percentage of Embryos with Buds

| BAP, mg/l | ABA, mg/l | | | | |
|---|---|---|---|---|---|
| | 0 | 0.03 | 0.3 | 3.0 | 30.0 |
| 10 | 40 | 55 | 80 | 50 | 44 |
| 20 | 60 | 90 | 44 | 44 | 0 |

TABLE 3

Bud Induction by Decoated Seeds with High Levels of BAP

| Growth Factor Concentration, mg/l | | Germinating Seeds with Buds, % | Total Germinating Seed |
|---|---|---|---|
| BAP | ABA | | |
| 10 | 0.03 | 100 | 4 |
| 10 | 0.3 | 0 | 3 |
| 10 | 3.0 | 0 | 1 |
| 20 | 0.03 | 0 | 1 |
| 20 | 0.3 | 100 | 1 |
| 20 | 3.0 | 50 | 2 |
| 30 | 0.3 | 100 | 2 |
| 30 | 0.3 | ND | 0 |
| 30 | 3.0 | 67 | 3 |
| 50 | 0.03 | 100 | 1 |
| 50 | 0.3 | 50 | 4 |
| 50 | 3.0 | 100 | 1 |

Data at 4 weeks in culture
ND = no data.

TABLE 4

Bud Production by Five Loblolly Pine Seed Families From
Decoated Seeds - Percentage of Embryos with Buds

| Growth Factor Concentrations, mg/l | | Seed Families | | | | |
|---|---|---|---|---|---|---|
| BAP | ABA | A | B | C | D | E |
| 20 | 0.03 | 100 | 83 | 83 | 100 | 67 |
| 10 | 0.3 | 50 | 75 | 100 | 75 | 100 |
| 1 | 3.0 | 83 | 43 | 75 | 40 | 60 |
| 20 | 0 | 71 | ND | ND | ND | ND |
| 10 | 0 | 80 | ND | ND | ND | ND |
| 1 | 0 | 27 | ND | ND | ND | ND |

Results after 40 days in culture
ND = no data

TABLE 5

BUD PRODUCTION BY FIVE LOBLOLLY PINE SEED FAMILIES WITH TIME IN CULTURE -
PERCENTAGE OF EMBRYOS WITH BUDS

| GROWTH FACTOR CONCENTRATION, mg/l | | SEED FAMILY | | | | | | | | | | | | | | | | | | | |
|---|---|---|---|---|---|---|---|---|---|---|---|---|---|---|---|---|---|---|---|---|---|
| | | A Weeks | | | | B Weeks | | | | C Weeks | | | | D Weeks | | | | E Weeks | | | |
| BAP | ABA | 2 | 3 | 4 | 5 | 2 | 3 | 4 | 5 | 2 | 3 | 4 | 5 | 2 | 3 | 4 | 5 | 2 | 3 | 4 | 5 |
| 20 | 0.03 | 10 | 38 | 38 | 75 | 0 | 0 | 20 | 67 | 0 | 0 | 30 | 50 | 0 | 0 | 11 | 50 | 10 | 10 | 11 | 33 |
| 10 | 0.3 | 11 | 25 | 25 | 28 | 0 | 0 | 30 | 50 | 10 | 10 | 50 | 100 | 0 | 0 | 25 | 75 | 0 | 11 | 33 | 50 |
| 1 | 3.0 | 0 | 0 | 12 | 25 | 0 | 0 | 20 | 29 | 0 | 0 | 11 | 25 | 0 | 0 | 12 | 40 | 0 | 0 | 10 | 20 |
| 20 | 0 | 0 | 0 | 40 | 71 | ND | ND | ND | ND | ND | ND | ND | ND | ND | ND | ND | ND | ND | ND | ND | ND |
| 10 | 0 | 0 | 11 | 11 | 40 | ND | ND | ND | ND | ND | ND | ND | ND | ND | ND | ND | ND | ND | ND | ND | ND |
| 1 | 0 | 0 | 0 | 0 | 0 | ND | ND | ND | ND | ND | ND | ND | ND | ND | ND | ND | ND | ND | ND | ND | ND |

ND = no data

Similarly excised embryos were cultured in similar media with specified concentrations of BAP and ABA. As seen in table 6, below, the bud induction effect of BAP and ABA was less pronounced for excised embryos than on stimulated decoated seeds.

TABLE 6

BUD INDUCTION RESPONSES OF WHOLE EXCISED
EMBRYOS AT THIRTY DAYS - PERCENTAGE
OF EMBRYOS WITH BUDS

| BAP, mg/l | ABA, mg/l | | |
|---|---|---|---|
| | 0.03 | 0.3 | 3.0 |
| 1.0 | 20 | 29 | 44 |
| 10.0 | 20 | 40 | 11 |
| 20.0 | 33 | 43 | 75 |

While specific examples relating to this invention have been described, it will be evident to those skilled in the art that other variations within the scope of the claims appended hereto are possible.

We claim:

1. A tissue culture method for asexually propagating loblolly pine trees comprising:
   stimulating pine seeds for germination;
   decoating the stimulated seeds;
   inoculating the decoated seeds on a culture medium containing from about 1 to 20 mg./l of benzylaminopurine and from 0 to 30 mg./l of abscisic acid to promote the formation of multiple adventitious buds that can be rooted to provide multiple plants from a single seed.

2. The method according to claim 1 wherein the seed stimulation is carried out by making a root end cut into the seed's endosperm and immersing the cut seed in a dilute hydrogen peroxide solution.

3. The method according to claim 2 wherein the culture medium contains from about 10 to 20 mg./l of benzylaminopurine and from about 0 to about 3 mg./l of abscisic acid.

4. The method according to claim 3 wherein the culture medium contains about 0.03 mg./l of abscisic acid.

5. The method according to claim 4 wherein the surface-sterilized seeds are inoculated into the culture medium by inserting the protruding root radical into the culture medium.

6. The method according to claim 1 wherein the surface-sterilized seeds are inoculated into the culture medium by inserting the protruding root radical into the culture medium.

7. The method according to claim 1 wherein the culture medium contains from about 10 to 20 mg./l of benzylaminopurine and from 0 to about 30 mg./l of abscisic acid.

8. The method according to claim 7 wherein the culture medium contains about 20 mg./l of benzylaminopurine.

9. The method according to claim 8 wherein the culture medium contains about 0.03 mg./l of abscisic acid.

10. The method according to claim 9 wherein the surface sterilized seeds are inoculated into the culture medium by inserting the protruding root radical into the medium.

11. A tissue culture medium for use in the promotion of multiple adventitious buds from decoated growth stimulated loblolly pine seeds or embryos or embryonic tissue excised from loblolly pine seeds comprising suitable nutrients, about 1 to 20 mg./l of benzylaminopurine and about 0.03 to 3.0 mg./l of abscisic acid.

12. The medium according to claim 11 wherein benzylaminopurine is at a concentration of from about 10 to 20 mg./l.

13. The medium according to claim 12 wherein the benzylaminopurine is at a concentration of about 20 mg./l.

14. The medium according to claim 13 wherein the abscisic acid is at a concentration of about 0.03 mg./l.

* * * * *